(12) United States Patent
Chomas et al.

(10) Patent No.: US 9,089,668 B2
(45) Date of Patent: Jul. 28, 2015

(54) FLOW DIRECTIONAL INFUSION DEVICE

(75) Inventors: James E. Chomas, Denver, CO (US); Norman R. Weldon, Evergreen, CO (US); Leonard Pinchuk, Miami, FL (US)

(73) Assignee: SUREFIRE MEDICAL, INC., Westminster, CO (US)

( * ) Notice: Subject to any disclaimer, the term of this patent is extended or adjusted under 35 U.S.C. 154(b) by 324 days.

(21) Appl. No.: 13/611,080

(22) Filed: Sep. 12, 2012

(65) Prior Publication Data
US 2013/0079731 A1 Mar. 28, 2013

Related U.S. Application Data

(60) Provisional application No. 61/540,109, filed on Sep. 28, 2011.

(51) Int. Cl.
*A61M 25/00* (2006.01)
*A61F 2/01* (2006.01)
(Continued)

(52) U.S. Cl.
CPC ...... *A61M 25/0043* (2013.01); *A61B 17/12113* (2013.01); *A61B 17/12186* (2013.01); *A61F 2/01* (2013.01); *A61M 25/0097* (2013.01); *A61B 2017/1205* (2013.01); *A61M 2039/2406* (2013.01); *A61M 2039/2433* (2013.01);
(Continued)

(58) Field of Classification Search
CPC ................ A61M 2039/2406; A61M 2205/75; A61M 2205/7545; A61M 2205/7554; A61M 2205/7563; A61M 2205/7572; A61M 2205/7581; A61M 25/0043; A61M 25/0054; A61B 17/12109; A61B 17/12113; A61B 2017/1205; A61F 2/01; A61F 2/013

USPC .......... 604/264, 266, 268, 96.01, 99.02, 104; 606/200
See application file for complete search history.

(56) References Cited

U.S. PATENT DOCUMENTS 4,738,740 A 4/1988 Pinchuk et al.
5,234,425 A 8/1993 Fogarty et al.
(Continued)

FOREIGN PATENT DOCUMENTS

| WO | WO 99/44510 A1 | 9/1999 |
| WO | WO 01/45592 A1 | 6/2001 |
| WO | WO 01/49215 A2 | 7/2001 |

OTHER PUBLICATIONS

Fusion Drug Delivery System-Novel Catheter/Stent Design for Targeted Drug Delivery, Gerschwind & Barnett, Non-Published US provisional patent application filed Sep. 17, 2007.
(Continued)

*Primary Examiner* — Bhisma Mehta
*Assistant Examiner* — Nilay Shah
(74) *Attorney, Agent, or Firm* — Gordon & Jacobson, PC

(57) ABSTRACT

A flow directional infusion device includes a filter valve located at the distal end of a catheter. The filter valve constrains delivery of an embolic agent through the catheter to the locus of the aneurysm. In order to provide such delivery, the valve includes a longitudinal opening, radial opening or is otherwise partially permeable in a direction of the aneurysm so that the embolic agent or a delivery element for such agent is limited toward the aneurysm. In addition, the filter valve permits and directs blood flow within the blood vessel about the aneurysm during the treatment without obstructing the vessel and without allowing retrograde flow of the embolic agent in the vessel upstream of the aneurysm.

17 Claims, 10 Drawing Sheets

(51) Int. Cl.
*A61B 17/12* (2006.01)
*A61M 39/24* (2006.01)

(52) U.S. Cl.
CPC .... *A61M2205/75* (2013.01); *A61M 2205/7545* (2013.01); *A61M 2205/7554* (2013.01)

(56) References Cited

U.S. PATENT DOCUMENTS

| | | |
|---|---|---|
| 5,893,869 A | 4/1999 | Barnhart et al. |
| 5,895,399 A | 4/1999 | Barbut et al. |
| 5,910,154 A | 6/1999 | Tsugita et al. |
| 5,911,734 A | 6/1999 | Tsugita et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,059,745 A | 5/2000 | Gelbfish |
| 6,152,946 A | 11/2000 | Broome et al. |
| 6,165,200 A | 12/2000 | Tsugita et al. |
| 6,168,579 B1 | 1/2001 | Tsugita |
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |
| 6,371,971 B1 | 4/2002 | Tsugita et al. |
| 6,383,206 B1 | 5/2002 | Gillick et al. |
| 6,395,014 B1 | 5/2002 | Macoviak et al. |
| 6,436,112 B2 | 8/2002 | Wensel et al. |
| 6,443,926 B1 | 9/2002 | Kletschka |
| 6,485,456 B1 | 11/2002 | Kletschka |
| 6,485,502 B2 | 11/2002 | Don Michael et al. |
| 6,499,487 B1 | 12/2002 | McKenzie et al. |
| 6,530,935 B2 | 3/2003 | Wensel et al. |
| 6,533,800 B1 | 3/2003 | Barbut |
| 6,537,294 B1 | 3/2003 | Boyle et al. |
| 6,537,297 B2 | 3/2003 | Tsugita et al. |
| 6,540,722 B1 | 4/2003 | Boyle et al. |
| 6,551,303 B1 | 4/2003 | Van Tassel et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang et al. |
| 6,645,220 B1 | 11/2003 | Huter et al. |
| 6,645,222 B1 | 11/2003 | Parodi et al. |
| 6,645,223 B2 | 11/2003 | Boyle et al. |
| 6,652,555 B1 | 11/2003 | VanTassel et al. |
| 6,652,556 B1 | 11/2003 | VanTassel et al. |
| 6,656,351 B2 | 12/2003 | Boyle |
| 6,673,090 B2 | 1/2004 | Root et al. |
| 6,676,682 B1 | 1/2004 | Tsugita et al. |
| 6,689,150 B1 | 2/2004 | VanTassel et al. |
| 6,692,508 B2 | 2/2004 | Wensel et al. |
| 6,692,509 B2 | 2/2004 | Wensel et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,702,834 B1 | 3/2004 | Boylan et al. |
| 6,706,053 B1 | 3/2004 | Boylan et al. |
| 6,706,055 B2 | 3/2004 | Douk et al. |
| 6,730,108 B2 | 5/2004 | VanTassel et al. |
| 6,746,469 B2 | 6/2004 | Mouw |
| 6,818,006 B2 | 11/2004 | Douk et al. |
| 6,830,579 B2 | 12/2004 | Barbut |
| 6,837,898 B2 | 1/2005 | Boyle et al. |
| 6,855,154 B2 | 2/2005 | Abdel-Gawwad |
| 6,866,677 B2 | 3/2005 | Douk et al. |
| 6,887,258 B2 | 5/2005 | Denison et al. |
| 6,896,690 B1 * | 5/2005 | Lambrecht et al. ........... 606/200 |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,936,060 B2 | 8/2005 | Hogendijk et al. |
| 6,939,362 B2 | 9/2005 | Boyle et al. |
| 6,964,670 B1 | 11/2005 | Shah et al. |
| 6,964,673 B2 | 11/2005 | Tsugita et al. |
| 6,974,469 B2 | 12/2005 | Broome et al. |
| 6,989,027 B2 | 1/2006 | Allen et al. |
| 7,044,958 B2 | 5/2006 | Douk et al. |
| 7,044,966 B2 | 5/2006 | Svanidze et al. |
| 7,066,946 B2 | 6/2006 | Douk et al. |
| 7,101,396 B2 | 9/2006 | Artof et al. |
| 7,162,303 B2 | 1/2007 | Levin et al. |
| 7,169,164 B2 | 1/2007 | Borillo et al. |
| 7,172,614 B2 | 2/2007 | Boyle et al. |
| 7,172,621 B2 | 2/2007 | Theron |
| 7,214,237 B2 | 5/2007 | Don Michael et al. |
| 7,217,255 B2 | 5/2007 | Boyle et al. |
| 7,223,253 B2 | 5/2007 | Hogendijk |
| 7,232,452 B2 | 6/2007 | Adams et al. |
| 7,232,453 B2 | 6/2007 | Shimon |
| 7,241,304 B2 * | 7/2007 | Boyle et al. ................... 606/200 |
| 7,250,041 B2 | 7/2007 | Chiu et al. |
| 7,252,675 B2 * | 8/2007 | Denison et al. ............... 606/200 |
| 7,279,000 B2 | 10/2007 | Cartier et al. |
| 7,306,575 B2 | 12/2007 | Barbut et al. |
| 7,322,957 B2 | 1/2008 | Kletschka et al. |
| 7,326,226 B2 | 2/2008 | Root et al. |
| 7,331,973 B2 | 2/2008 | Gesswein et al. |
| 7,338,510 B2 | 3/2008 | Boylan et al. |
| 7,344,549 B2 | 3/2008 | Boyle et al. |
| 7,371,249 B2 | 5/2008 | Douk et al. |
| 7,425,215 B2 | 9/2008 | Boyle et al. |
| 7,537,600 B2 | 5/2009 | Eskuri |
| 7,544,202 B2 | 6/2009 | Cartier et al. |
| 7,572,272 B2 | 8/2009 | Denison et al. |
| 7,582,100 B2 | 9/2009 | Johnson et al. |
| 7,585,309 B2 | 9/2009 | Larson |
| 7,591,832 B2 | 9/2009 | Eversull et al. |
| 7,604,649 B2 * | 10/2009 | McGuckin et al. ........... 606/200 |
| 7,604,650 B2 | 10/2009 | Bergheim |
| 7,621,935 B2 * | 11/2009 | Saito et al. .................... 606/200 |
| 7,647,115 B2 | 1/2010 | Levin et al. |
| 7,653,438 B2 | 1/2010 | Deem et al. |
| 7,842,084 B2 | 11/2010 | Bicer |
| 7,853,333 B2 | 12/2010 | Demarais |
| 7,873,417 B2 | 1/2011 | Demarais |
| 7,937,143 B2 | 5/2011 | Demarais et al. |
| 2002/0161394 A1 | 10/2002 | Macoviak et al. |
| 2003/0187474 A1 | 10/2003 | Keegan et al. |
| 2004/0220609 A1 | 11/2004 | Douk et al. |
| 2005/0015048 A1 | 1/2005 | Chiu et al. |
| 2005/0015112 A1 | 1/2005 | Cohn et al. |
| 2005/0261759 A1 | 11/2005 | Lambrecht et al. |
| 2006/0173490 A1 | 8/2006 | LaFontaine et al. |
| 2007/0179590 A1 | 8/2007 | Lu et al. |
| 2008/0033341 A1 * | 2/2008 | Grad ............................. 604/20 |
| 2008/0039786 A1 | 2/2008 | Epstein et al. |
| 2009/0018498 A1 | 1/2009 | Chiu et al. |
| 2009/0076409 A1 | 3/2009 | Wu et al. |
| 2011/0137399 A1 * | 6/2011 | Chomas et al. .............. 623/1.12 |

OTHER PUBLICATIONS

A Study of the Geometrical and Mechanical Properties of a Self-Expandig Metallic Stent—Theory and Experiment, Dr. Michael R. Jedwab, Claude O. Clerc, Journal of Applied Biomaterials, vol. 4, Issue 1, pp. 77-85, Spring 1993.

Finite Element Stent Design, M. De Beule, R. Van Impe, P. Verdonck, B. Verhegghe, Computer Methods in Biomechanics and Biomedical Engineering, 2005.

Catheter-Based Renal Sympathetic Denervation for Resistant Hypertension: a Multicentre Safety and Proof-of-Principle Cohort Study, Krum et al, The Lancet, 2009.

(56) References Cited

OTHER PUBLICATIONS

Renal Denervation as a Therapeutic Approach for Hypertension: Novel Implications for an Old Concept, Schlaich et al., Hypertension, Journal of the American Heart Association, 2009, 54:1195-1201.

Renal Sympathetic-Nerve Ablation for Uncontrolled Hypertension, Schlaich et al, The New England Journal of Medicine, 2009, pp. 932-934.
US 7,169,126, 01/2007, Zadno-Azizi (withdrawn)

\* cited by examiner

FLOW DIRECTIONAL INFUSION DEVICE

CROSS-REFERENCE TO RELATED APPLICATION

This application claims the benefit of U.S. Ser. No. 61/540,109, filed Sep. 28, 2011, which is hereby incorporated by reference herein in its entirety.

BACKGROUND OF THE INVENTION

1. Field of the Invention

The present invention relates to methods and systems for treating blood vessels. More particularly, the invention relates to methods and systems for treating vascular malformations, such as aneurysms. Even more particularly, the present invention relates to methods and systems for treating an aneurysm with a microcatheter and an embolic agent.

2. State of the Art

An aneurysm is a localized, blood-filled balloon-like bulge in the wall of a blood vessel. Aneurysms can commonly occur in arteries at the base of the brain, i.e., at the circle of Willis. Another common type of aneurysm is an aortic aneurysm in the main artery carrying blood from the left ventricle of the heart.

The development of an aneurysm causes a turbulent blood flow within the vessel localized at bulge which in turn increases wall stress at bulge and consequent increased dilation. In hemodynamic terms, the coupling of aneurysmal dilatation and increased wall stress is approximated by the Law of Laplace. The Law of Laplace applied to a cylinder states that the (arterial) wall tension is equal to the pressure times the radius of the arterial conduit ($T=P \times R$). As diameter increases, wall tension increases, which contributes to more increase in diameter. When the size of an aneurysm increases, there is a significant risk of rupture, resulting in severe hemorrhage, other complications or death. Eventually all aneurysms will, if left to complete their evolution, rupture without intervention. Current treatments seek to fill the aneurism to thereby reduce the wall stress at the aneurysm in response to the stress induced as the blood flows through the vessel.

In one method, a microcatheter is advanced directly into the aneurysm, and embolic beads or other embolic agents are infused directly into the aneurysm. However, infusion with a standard microcatheter routinely leads to non-targeted delivery of the embolic agent, either downstream (antegrade) or backwards (reflux), which can lead to mild to severe complications.

Another method of treatment includes placing a stent in the blood vessel across the aneurysm. Once the vessel is stented, a catheter is advanced through the stent and laterally into the aneurysm. With the catheter in position, endovascular coils are advanced from the catheter and into the aneurysm until no additional coils can be placed; i.e., the aneurysm is completely occluded with the coils flush with the vessel wall and outer surface of the stent. The coils initiate a clotting or thrombotic reaction within the aneurysm that, when successful, eliminates the aneurysm. An advantage of this method is that it can be performed without occluding the blood vessel to blood flow. The stent separates the occlusion zone from the blood flow within the vessel and blood flow is maintained while the coils are advanced into the aneurism. However, the method is only suitable for use on larger vessels that can accommodate being stented. In addition, the method requires that the stent remain implanted permanently. It is generally undesirable to have a permanent implant where an option exists for treatment without an implant.

It is also known to treat an aneurysm by filling the aneurysm with a slow setting liquid embolic agent such as ethylene vinyl alcohol copolymer dissolved in the organic solvent dimethyl sulfoxide (DMSO). Such an liquid embolic agent is available from EV3 of Irvine, Calif. under the brand ONYX™. Such current method includes positioning a PTFE balloon within the blood vessel so that it extends across the aneurysm. A microcatheter is also positioned within the blood vessel and enters the aneurysm. Such microcatheter may extend alongside the balloon or be partly carried by the balloon. The balloon is inflated to segregate the aneurysm from the blood vessel, and the liquid embolic agent is injected through the microcatheter into the aneurysm. As the aneurysm is filled with the embolic agent, the balloon keeps the embolic agent within the aneurysm. The microcatheter is withdrawn once the aneurysm is filled. Once the embolic agent cures, the balloon is removed. The balloon defines a very smooth repair to the vessel wall. A successful treatment operates to reduce the wall stress at the aneurism. However, because the balloon completely occludes blood flow during the treatment and the liquid agent requires a significant amount of time to set as a solid, there is the opportunity for inducing a local ischemic event due to a lack of blood supply during the treatment time.

SUMMARY OF THE INVENTION

A flow directional infusion device includes a catheter operating in conjunction with a filter valve. An embolic agent in the form of beads, liquid, coils, or any other suitable form can be delivered through the catheter. The filter valve is located adjacent a distal end portion of the catheter and includes a passage between the proximal and distal ends of the filter valve through which the embolic agent can be delivered. The filter valve constrains delivery of the embolic agent to the locus of the aneurysm. In addition, the filter valve permits and directs blood flow within the blood vessel about the aneurysm during the treatment without obstructing the vessel and without allowing retrograde flow of the embolic agent in the vessel upstream of the aneurysm. To that end, the filter valve dynamically moves within the vessel between an expanded valve-open configuration and a collapsed valve-closed configuration depending on the local blood flow conditions about the valve within the blood vessel. When the filter valve is in the valve-open configuration the filter valve is impermeable to the embolic agent, and when the filter valve is in the valve-closed position the filter valve permits antegrade blood flow about the filter valve. The filter valve preferably automatically expands from the valve-closed configuration to the valve-open configuration in less than one second, and more preferably less than one-tenth of second, in an at-rest fluid having a viscosity approximating the viscosity of blood. In addition, the filter valve automatically collapses into the valve-closed configuration during systole and automatically expands into the valve-open configuration during diastole and low flow conditions.

One manner of achieving the rapid transition required between valve-open and valve-closed states is via a preferred construction of the filter valve. The valve is preferably made from a plurality of elongate first filaments each having a diameter of 0.025 mm to 0.127 mm. These filaments may be round in cross-section, flat in cross-section, may be formed in pairs of filaments, or other means of reducing the wall thickness of the filter valve. In addition, in the valve-open configuration, the first filaments preferably cross one another at an angle of 100° to 150°, and said first filaments preferably have a Young's modulus of elasticity greater than 100 MPa.

In addition, a filter is provided to the braided first filaments. The filter is preferably formed by electrostatically depositing or spinning polymeric second filaments onto the braided first filaments. The deposition of the second filaments preferably defines a pore size in the filter not exceeding 500 µm.

In certain embodiments, first filaments are secured relative to each other about the distal end of the catheter. Such catheter to which the proximal ends of the first filaments are secured may either be a delivery catheter through which an injection microcatheter extends, or the distal end of the microcatheter itself, as described herein. The remaining length of the braided first filaments are non-fixed relative to each other such that the first filaments are movable relative to each other. The valve is expandable from the valve-closed configuration to the valve-open configuration by way of an inherent spring-bias of the first filaments which biases the first filaments radially apart from one another so as to flare outward relative to their secured proximal ends. The filaments may define a radial or other lateral opening for lateral passage of a portion of the microcatheter outside the filter valve and into the aneurysm. The lateral opening may be formed by an elongate opening, such as a slit in the valve or break in the filaments, extending completely from the proximal to distal ends of the valve, or may be an opening defined along of portion of the valve extending partially between, but not fully along the length of the valve.

In other embodiments, both the proximal ends of the first filaments are secured relative to each other at the distal end of a catheter, and the distal ends of the first filaments are secured relative to each other at a distally displaced location relative to the distal end of the catheter such that the braid of first filaments extends between the first and second hubs in a tubular form. The filter of second filaments is applied to the braid of first filaments between their first and second ends about an axis of rotation less than 360° around the tubular form and thereby defining a non-filtering portion of the valve about at least a portion of the braid of first filaments intended to face the aneurysm during injection of an embolic agent. In this manner, the non-filtering portion of the valve is permeable to the embolic agent permitting embolic agent transfer from within the space defined by the tubular form of the braid of first filaments into the aneurysm in a directed manner. Where a tubular form braid is defined, the ends of the first filaments may be coupled at their proximal and/or distal ends to a respective hub. The distal hub is particular useful to allow physical displacement of the distal ends of the first filaments relative to the proximal ends in order to elongate the filter valve and minimize its diameter during insertion into the blood vessel. The distal hub may include a self-closing valve, permitting the embolic agent to be injected through the catheter and then directed out of the agent-permeable portion of the filter valve. Alternatively, the distal hub may not be sealed, and a second smaller catheter (microcatheter) is advanced through the catheter and directed to inject the embolic agent toward the agent-permeable portion of the filter valve and into the aneurysm. The microcatheter may be advanced completely through an opening in the filamentary braid to assist in placement of the embolic agent within the aneurysm and thereafter withdrawn. Alternatively, the microcatheter may be formed to direct the embolic agent at an appropriate course into the aneurysm while the microcatheter remains located within the braid. The braid is biased to expand outward and upon systolic conditions of anterograde blood flow automatically radially collapses into the valve-closed configuration, and during diastolic conditions of retrograde fluid flow and low flow conditions, automatically radially expand to permit the filter to capture any embolic agent from backflow within the vessel.

In the latter embodiments, an elongate member is insertable into the catheter and to the distal hub, to contact a portion of the distal hub and displace the distal hub relative to the proximal hub to forcibly reduce the valve filter diameter to aid in advancement of the valve filter into the blood vessel. Such elongate member may be removable from the catheter to allow automatic operation of the valve filter. Alternatively, the microcatheter may function as the elongate member.

DETAILED DESCRIPTION OF THE PREFERRED EMBODIMENTS

Figure 1:
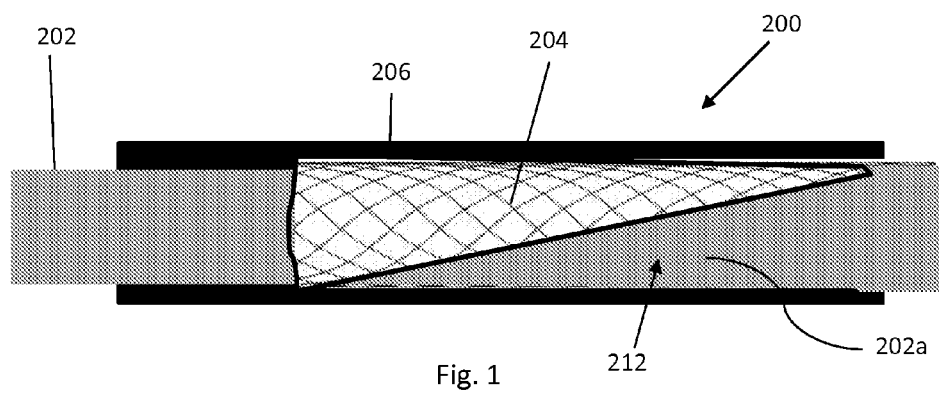
FIG. 1 is a schematic broken side view of a first embodiment of a flow directional infusion device according to the invention, shown in a non-deployed configuration.
Figure 2:
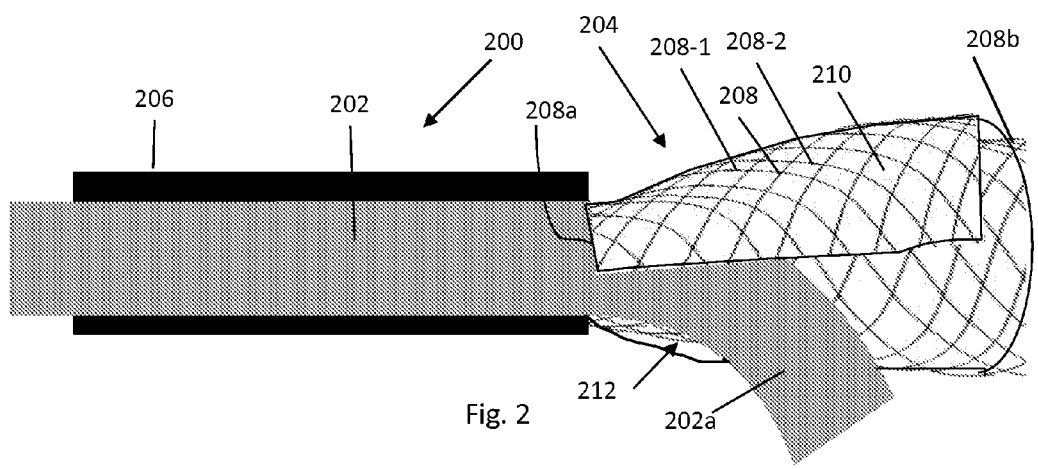
FIG. 2 is a schematic broken side view of the first embodiment of a flow directional infusion device according to the invention, shown in a deployed configuration.

Referring to FIGS. 1 and 2, a first exemplary embodiment of a flow directional infusion device 200 according to the invention is shown. The flow directional infusion device 200 includes a catheter 202 operating in conjunction with a filter valve 204.

It should be appreciated by those skilled in the art that the catheter 202 can be any catheter known in the art. Typically, the catheter will be between two and eight feet long, have an outer diameter of between 0.67 mm and 3 mm (corresponding to catheter sizes 2 French to 9 French), and will be made from a liner made of fluorinated polymer such as polytetrafluoroethylene (PTFE) or fluorinated ethylene propylene (FEP), a braid made of metal such as stainless steel or titanium, or a polymer such as polyethylene terephthalate (PET) or liquid crystal polymer, and an outer coating made of a polyether block amide thermoplastic elastomeric resin such as PEBAX®, polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream.

The catheter 202 is preferably provided with a sleeve or outer catheter 206 comprised of a material capable of holding the valve 204 in a cylindrical space over the catheter 202 and capable of sliding over the valve 204 and the catheter 202. The sleeve or outer catheter 206 can be comprised of polyurethane, polyamide, copolymers of polyamide, polyester, copolymers of polyester, fluorinated polymers, such as PTFE, FEP, polyimides, polycarbonate or any other suitable material. The sleeve or outer catheter 206 may also contain a braid composed of metal such as stainless steel or titanium, or a polymer such as PET or liquid crystal polymer, or any other suitable material. The wall thickness of sleeve or outer catheter 206 is preferably in the range of 0.05 mm to 0.25 mm with a more preferred thickness of 0.1 mm-0.15 mm.

The valve 204 is comprised of one, two, or more metal (e.g., stainless steel or Nitinol) or polymer first filaments 208, which form a substantially frustoconical shape when not subject to outside forces. The filaments may be round in cross-section, flat in cross-section, may be formed in pairs of filaments, or other means of reducing the wall thickness of the valve. Where polymeric filaments are utilized, the filaments may be comprised of PET, polyethylene-napthalate (PEN), liquid crystal polymer, fluorinated polymers, nylon, polyamide or any other suitable polymer. If desired, when polymeric filaments are utilized, one or more metal filaments may be utilized in conjunction with the polymeric filaments. According to one aspect of the invention, where a metal filament is utilized, it may be of radio-opaque material such that it may be tracked in the body. The valve is capable of expanding in diameter while reducing in length, and reducing in diameter while expanding in length. The valve is preferably comprised of shape memory material that is formed and set in a large diameter orientation. As previously mentioned, the valve is preferably held in a small diameter orientation until it is released, and when released by removing the sleeve or other restricting component 206, the distal end of the valve expands to a larger diameter. In an embodiment in which the valve is comprised of multiple first filaments 208-1, 208-2, the proximal ends 208a of the filaments 208 may be constrained relative to each other and the catheter 202. It is preferred that the filaments not be bonded to each other along their lengths or at their distal ends 208b so to enable the valve to rapidly automatically open and close in response to dynamic flow conditions, as hereinafter described.

In the preferred embodiment, the valve 204 is constrained only at its proximal end where it is coupled to the catheter 202, while the remainder of the valve can either be constrained (retracted state) by the sleeve or catheter 206, or partially unconstrained (partially deployed state) or completely unconstrained (completely deployed state). When in the partially or completely unconstrained conditions, depending upon the flow conditions in the vessel, the valve 204 may either reach the walls of the vessel or it may not.

As previously mentioned, the filter valve diameter should automatically change in response to local flow conditions so as to enable forward flow, but capture embolic agents in brief or prolonged periods of reverse flow. For simplicity, the valve can be considered to exist in two conditions. In a "closed" condition, the valve is not sealed against the vessel wall and blood may flow around in at least a proximal to distal direction. In an "open" condition, the valve expands against the vessel wall 102 and blood must pass the valve if it is to flow past the valve within the vessel in either direction; in the "open" condition embolic agent is prevented from passing upstream (or in a distal to proximal direction) of the valve (FIG. 3).

At least three parameters help define the performance and novel nature of the valve: the radial (outward) force of the valve, the time constant over which the valve changes condition from closed to open, and the pore size of the valve.

Figure 3:
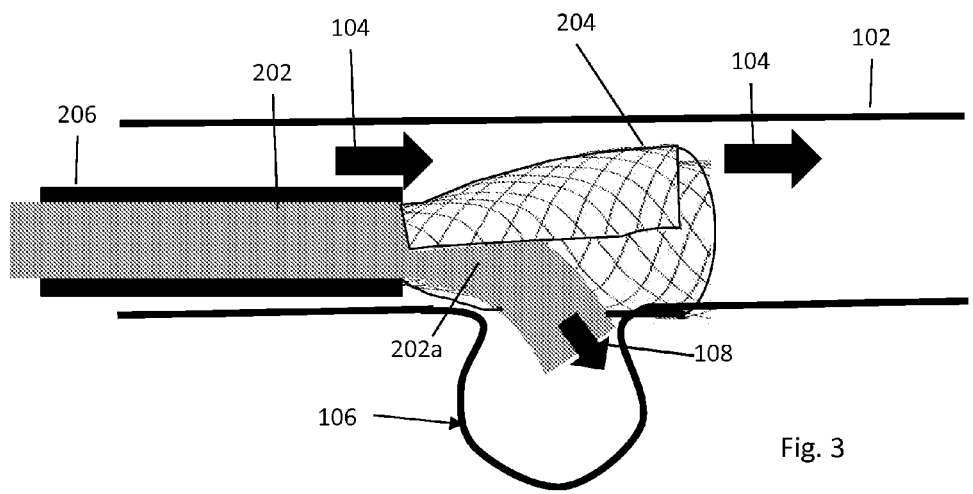
FIG. 3 is a schematic broken view of the first embodiment of a flow directional infusion device according to the invention, shown deployed within a blood vessel having an aneurysm and configured to inject an embolic agent into the aneurysm.
Figure 4A:
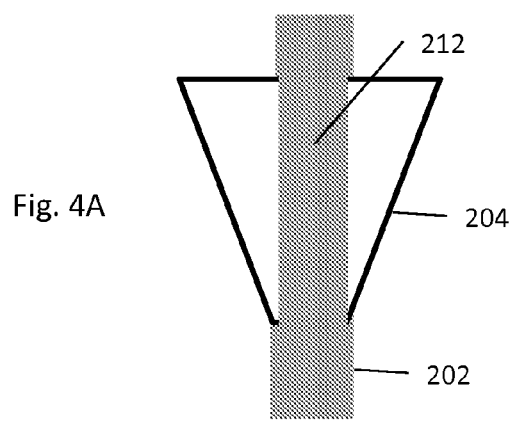
FIGS. 4A and 4B, show bottom and side schematic views, respectively, of one exemplar filter valve configuration for use with the first embodiment of the flow directional infusion device according to the invention.
Figure 4B:
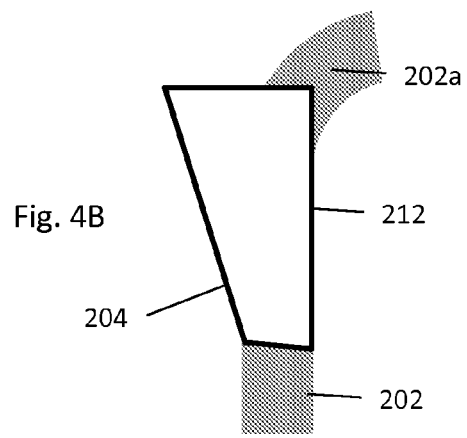

Referring to FIG. 3, in a preferred embodiment, the valve 204 expands fully to the vessel wall 102 (i.e., reaches an open condition) when any part of the flow around the braid nears stasis and remains in a closed condition when blood is flowing distally or downstream with regular force in the distal direction, as shown by the direction of arrows 104. More particularly, when the radial force of expansion of the valve 204 is greater than the force from forward blood flow 104, the valve expands to the vessel wall 102. However, according to one aspect of the invention, the radial force of expansion of the valve 204 is chosen to be low (as described in more detail below) so that blood flow in the distal (or downstream) direction will prevent the valve 204 from reaching the open condition. This is a relatively low expansion force compared to prior art stents, stent grafts, distal protection filters and other vascular devices, which have a sufficiently high radial force to fully expand to the vessel wall in all flow conditions.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

In one embodiment, with a valve arrangement as shown in FIG. 2, the valve 204 is composed of twenty-four polyethylene terephthalate (PET) filaments 208-1, 208-2, . . . , each having a diameter of 0.1 mm and pre-formed to an 8 mm diameter mandrel and a braid angle of 130° (i.e., the filaments are spring-biased or have a shape memory to assume an angle of 130° relative to each other when the valve assumes a fully deployed state and opens in a frustoconical configuration). The filaments (generally 208) preferably have a Young's modulus greater than 200 MPa, and the valve preferably has a radial force of less than 40 mN in the fully deployed position (i.e., where the filaments assume their shape memory). More preferably, the valve 204 has a radial force in the fully deployed position of less than 20 mN, and even more preferably the valve has a radial force of approximately 10 mN (where the term "approximately" as used herein is defined to mean±20%) in the deployed position, and yet even more preferably a radial force of approximately 5 mN. This compares to prior art embolic capture devices such as the ANGIO-GUARD® (a trademark of Cordis Corporation) and prior art Nitinol stents and stent-grafts which typically have radial forces of between 40 mN and 100 mN in their fully deployed positions.

According to one aspect of the invention, the valve 204 opens and closes sufficiently quickly to achieve high capture efficiency of embolic agents in the presence of rapidly changing flow direction. In one embodiment, the valve 204 moves from a fully closed (undeployed) position to a fully open position in a static fluid (e.g., glycerin) having a viscosity approximately equal to the viscosity of blood (i.e., approximately 3.2 cP) in 0.067 second. For purposes herein, the time it takes to move from the fully closed position to the fully open position in a static fluid is called the "time constant". According to another aspect of the invention, the valve 204 is arranged such that the time constant of the valve in a fluid having the viscosity of blood is between 0.01 seconds and 1.00 seconds. More preferably, the valve 204 is arranged such that the time constant of the valve in a fluid having the viscosity of blood is between 0.05 and 0.50 seconds. The time constant of the valve may be adjusted by changing one or more of the parameters described above (e.g., the number of filaments, the modulus of elasticity of the filaments, the diameter of the filaments, etc.).

As will be appreciated by those skilled in the art, the braid geometry of filaments 208-1, 208-2, etc., and the material properties thereof are intimately related to the radial force and time constant of the valve 204. Since, according to one aspect of the invention, the valve is useful in a variety of arteries of different diameters and flow conditions, each implementation can have a unique optimization. By way of example only, in one embodiment, the valve has ten filaments, whereas in another embodiment, the valve has forty filaments. Preferably, the filament diameter is chosen in the range of 0.025 mm to 0.127 mm, although other diameters may be utilized. Preferably, the pitch angle (i.e., the crossing angle assumed by the filaments in the fully open position—the shape memory position) is chosen in the range of 100° to 150°, although other pitch angles may be used. Preferably, the Young's modulus of the filament is at least 100 MPa, and more preferably at least 200 MPa.

According to another aspect of the invention, a filter structure 210 is formed on the braided filament structure (or filaments 208) to form a composite filter valve 204. The schematic illustrations are intended to indicate such a composite filter valve. The filter 210 can be placed onto the braid structure of filaments 208 by spraying, spinning, electrospinning, bonding with an adhesive, thermally fusing, mechanically capturing the braid, melt bonding, or any other desired method. The filter 210 can either be a material with pores such as ePTFE, a solid material that has pores added such as polyurethane with laser drilled holes, or the filter can be a web of very thin second filaments that are laid onto the braid. Where the filter is a web of thin second filaments, the characteristic pore size of the filter can be determined by attempting to pass beads of different diameters through the filter and finding which diameter beads are capable of passing through the filter in large quantities. The very thin second filaments can be spun onto a rotating mandrel with the aid of an electrostatic field or in the absence of an electrostatic field or both. Electrospinning of filaments with the aid of an electrostatic field is described in U.S. Pat. No. 4,738,740, which is hereby incorporated by reference herein. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In the preferred embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In an embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process.

According to one aspect of the invention, the filter 210 of the filter valve 204 has a characteristic pore size between 10 µm and 500 µm. More preferably, the filter portion has a characteristic pore size between 15 µm and 100 µm. Even more preferably, the filter portion 210 has a characteristic pore size of less than 40 µm and more preferably between 20 µm and 40 µm. Optionally, the filter portion 210 is provided with a characteristic pore size that will permit blood and contrast agent to pass therethrough while blocking passage of embolizing agent therethrough. However, it is appreciated that the filter need not be constructed to allow either blood or contrast agent to pass through in the upstream 'reflux' direction.

Figure 5A:
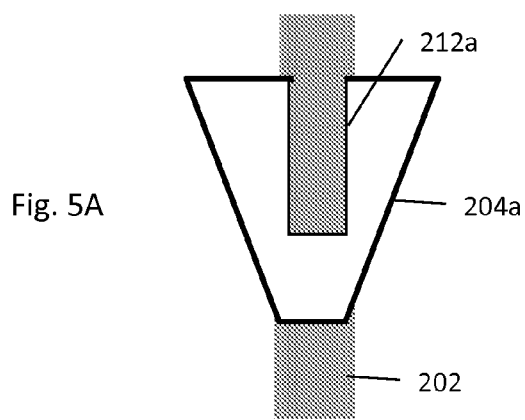
FIGS. 5A and 5B, show bottom and side schematic views, respectively, of a second exemplar filter valve configuration for use with the first embodiment of the flow directional infusion device according to the invention.
Figure 5B:
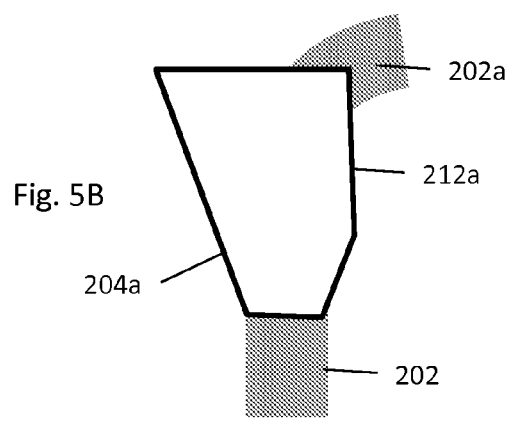
Figure 6A:
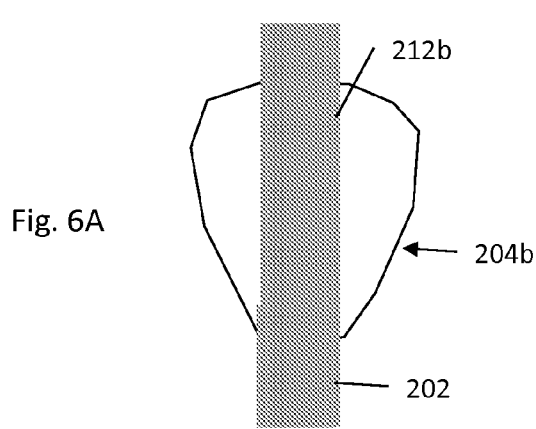
FIGS. 6A and 6B, show bottom and side schematic views, respectively, of a third exemplar filter valve configuration for use with the first embodiment of the flow directional infusion device according to the invention.
Figure 6B:
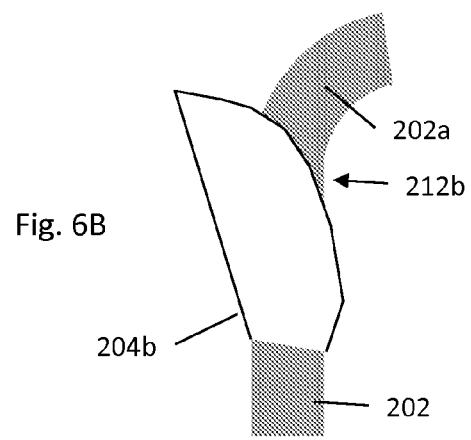

In accord with one aspect of the invention, the filter valve 204 includes a longitudinal opening (or circumferential discontinuity) 212 located between its proximal and distal ends; i.e., at a location somewhere between the proximal ends 208a of the first filaments 208 and the distal free ends 208b of the first filaments. In the embodiment shown in FIGS. 1 and 2, the proximal end of the filter valve is attached adjacent to, but proximally displaced from, the distal end of the catheter 202 and the filter valve 204 in the closed configuration extends along a distal portion 202a of the catheter. The filter valve 204 forms a generally conical skirt in the expanded open-configuration with a longitudinal opening 212 provided along the entire length of the filter valve between the proximal and distal ends of the filter valve. Referring to FIGS. 5A and 5B, in another embodiment, the filter valve 204a forms a generally conical skirt in the expanded open-configuration with the longitudinal opening 212a provided along only a distal portion of the length of the filter between the proximal and distal ends of the filter valve. Referring to FIGS. 6A and 6B, in yet another embodiment, the filter valve 204b forms a skirt with rounded ends generally in a tear-drop shape in the expanded open-configuration with the longitudinal opening 212b provided along the entire length of the filter valve between the proximal and distal ends of the filter valve. Referring to each of FIGS. 3, 4B, 5B and 6B, the respective longitudinal opening 212, 212a, 212b defines a passage for lateral displacement of the distal portion 202a of the catheter 202 outside the filter valve. To effect such lateral displacement the catheter 202 is preferably torqueable or otherwise steerable.

Turning back to FIG. 3, during use, the flow directional infusion device 200 is advanced into the blood vessel 102 to the locus of the aneurysm 106 in the non-deployed configuration; i.e., with the sleeve 206 extending about the distal portion 202a of the catheter 202 so as to constrain the filter valve 204 about the distal portion of the catheter. The infusion device 200 may be advanced to the desired location in a patient by any method known in the art. By way of example, a standard guidewire (not shown) can be advanced through the vasculature of the patient to a desired location of treatment. A delivery catheter (not shown) can then be advanced over the standard guidewire to the desired location. Once the delivery catheter is at the desired location, the standard guidewire is removed from the delivery catheter and patient. The infusion device 200 is then advanced through the delivery catheter. Alternatively, the infusion device 200 is advanced directly over the guidewire without the use of a delivery catheter.

Once the distal portion of the infusion device is at the proper location (preferably relatively coextending with the aneurysm 106), the catheter 202 and sleeve 206 are longitudinally displaceable relative to each other to effect retraction of the sleeve 206 from the filter valve 204 permitting the filter valve to operate in accord with its inherent properties, described above. As will be appreciated, sleeve retraction can be accomplished with a dedicated handle (not shown) that is coupled to the proximal ends of the each of the catheter 202 and the sleeve 206 (e.g., when the sleeve is an outer catheter or via a control member such as a wire extends between the sleeve and the handle) and facilitates such respective movement, or by having the proximal ends of the respective components manually displaceable by an operator. As shown in FIG. 3, with the sleeve 206 retracted, the filter valve 204 will, in accord with the spring bias of the first filaments 208, expand radially outward into the deployed configuration toward the wall of the vessel 102. During forward flow of blood in the direction of arrows 104, such as occurs during systole, the force of the blood is sufficient to cause the filter valve 204 to automatically radially compress at at least a portion thereof to permit flow of blood past the filter valve such that the filter valve does not obstruct blood flow. During low flow or retrograde flow conditions, such as occurs during diastole, the filter valve 204 automatically expands into the valve-open configuration again reaching the vessel wall 102 to thereby prevent upstream flow past the filter valve.

As also shown FIG. 3, with the infusion device at the proper location, the distal portion 202a of the catheter can be advanced through the longitudinal opening 212 in the filter valve 204 and into the aneurysm 106. In order to effect such advancement, the distal portion 202a of the catheter 202 is steered from its proximal end or via a guidewire, or has a pre-defined radial bias. Alternatively, the catheter may be without such steerable characteristic and guided toward the aneurysm 106 with the delivery catheter or via trial-and-error. Once the distal portion 202a of the catheter 202 is directed toward or more preferably located within the aneurysm 106, embolic agents are infused through the catheter and into the aneurysm as represented by arrow 108. Such embolic agents preferably comprise chemical agents including liquids, beads, gels, glues or any other suitable form that can be delivered through the catheter and operate to provide the desired treatment at the aneurysm. After the aneurysm 106 is treated, the sleeve 206 is moved relative to the catheter 202 to constrain the filter valve 204 about the distal portion of the catheter for withdrawal of the infusion device from the patient. Alternatively, the device is withdrawn without prior replacement of the sleeve 206 over the filter valve 204.

Figure 7:
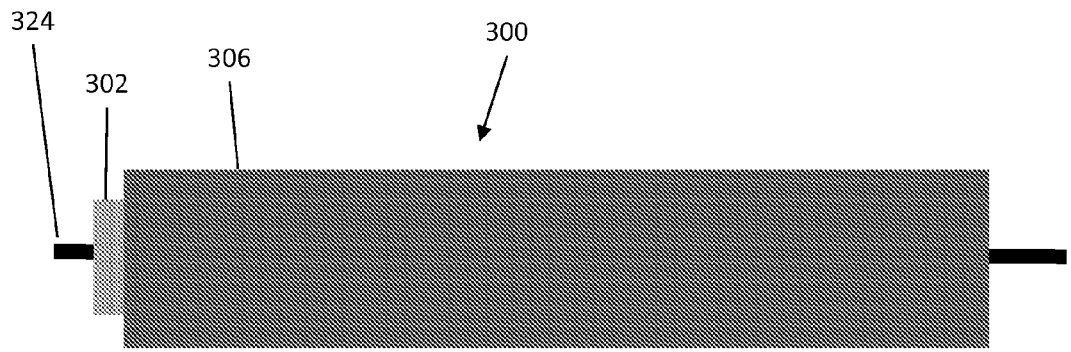
FIG. 7 is a schematic broken side view of a second embodiment of a flow directional infusion device according to the invention, shown in a non-deployed configuration.
Figure 8:
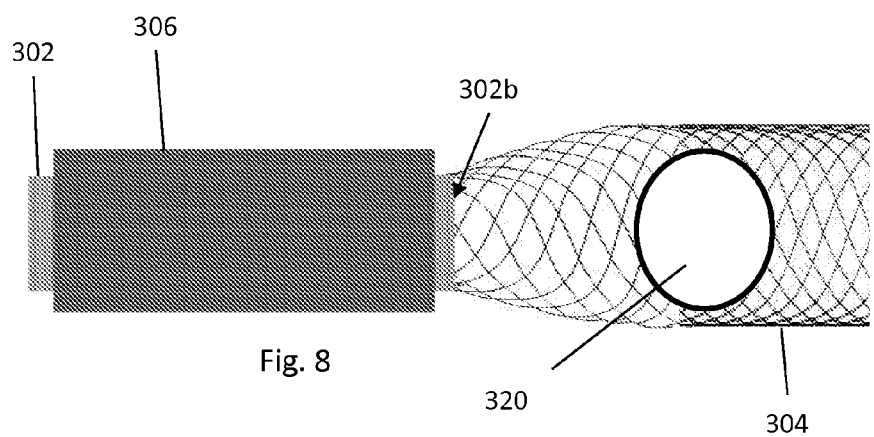
FIG. 8 is a schematic broken side view of the second embodiment of a flow directional infusion device according to the invention, shown in a deployed configuration.
Figure 9:
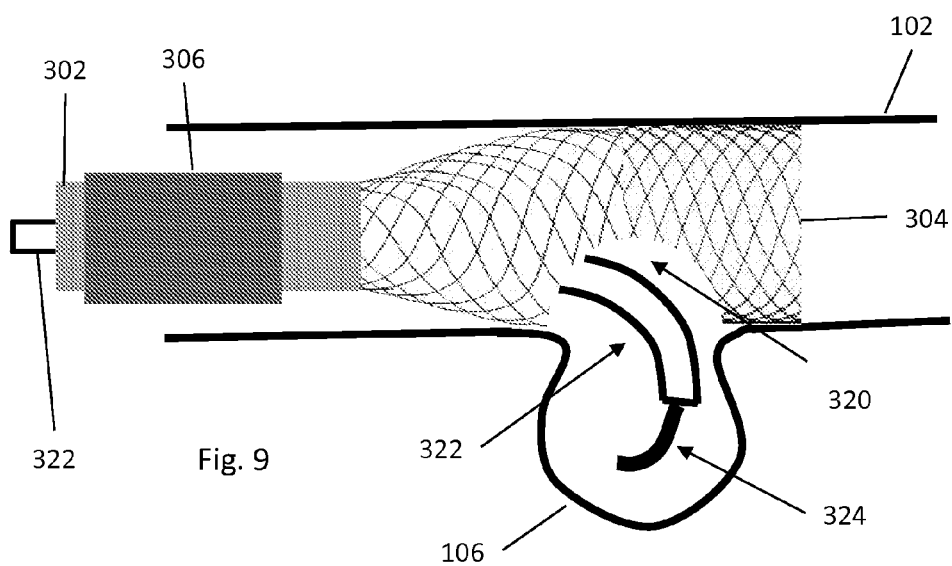
FIG. 9 is a schematic broken side view of the second embodiment of a flow directional infusion device according to the invention, shown deployed within a blood vessel having an aneurysm and configured to inject an embolic agent into the aneurysm.
Figure 10:
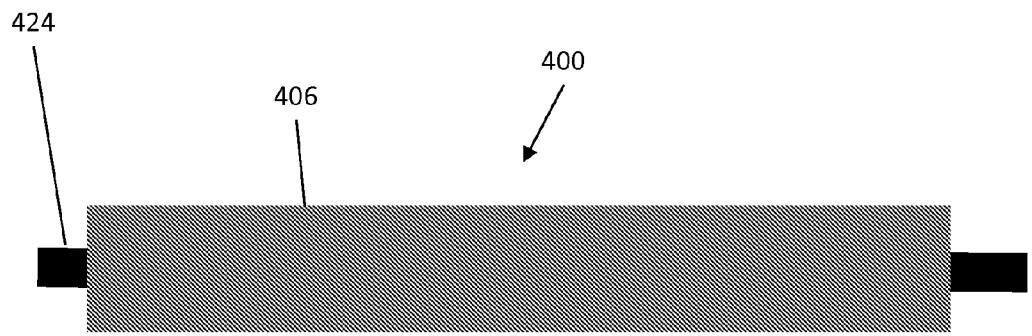
FIG. 10 is a schematic broken side view of a third embodiment of a flow directional infusion device according to the invention, shown in a non-deployed configuration.
Figure 11:
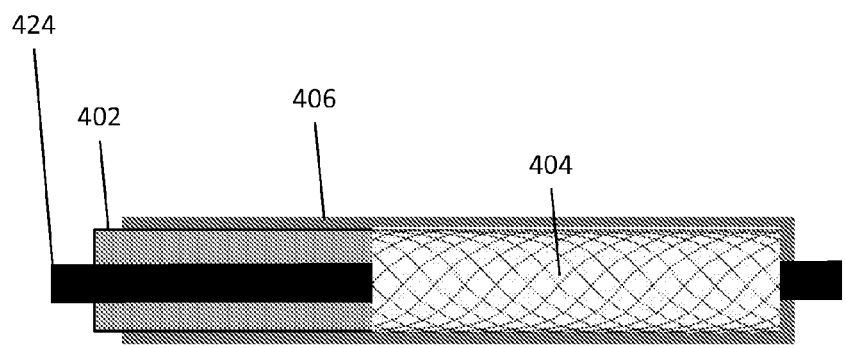
FIG. 11 is a schematic broken longitudinal section view similar to FIG. 10.

Turning now to FIGS. 7 through 9, a second embodiment of an infusion device 300 is shown. The device 300 includes a catheter 302, a filter valve 304, and an outer catheter or sleeve 306 displaceable relative to the catheter 302 and filter valve 304. The filter valve 304 is secured to the distal end 302b of the catheter 302, preferably with no portion of the catheter extending through the filter valve. The filter valve 304 is not necessarily provided with a longitudinal opening of the type described above. Rather, the filter valve in expanded tubular form defines a radial opening 320, such as in the shape of a round or oval hole.

A microcatheter 322 is provided for advancement through the catheter 302 and into the filter valve 304. The microcatheter 322 can be advanced through the radial opening 320 and into the aneurysm 106 in the vessel wall 102. A guidewire 324 may additionally be advanced within the microcatheter 322 to steer the microcatheter through the radial opening 320 and into the aneurysm 106.

In use, once the infusion device is at the proper location (preferably relatively coextending with the aneurysm 106), the catheter 302 and sleeve 306 are longitudinally displaceable relative to each other to effect retraction of the sleeve 306 from the filter valve 304 and thereby permitting the filter valve to operate in accord with its inherent properties, described above. As shown in FIG. 9, with the sleeve 306 retracted, the filter valve 304 will, in accord with its spring bias, expand radially outward to the wall of the vessel 102. During forward flow of blood, the force of the blood is sufficient to cause the filter valve 304 to automatically radially compress at at least a portion thereof to permit flow of blood past the filter valve such that the filter valve does not obstruct blood flow. During low flow or retrograde flow conditions, the filter valve 304 automatically expands into the valve-open configuration again reaching the vessel wall 102 to thereby prevent upstream flow past the filter valve.

Figure 12:
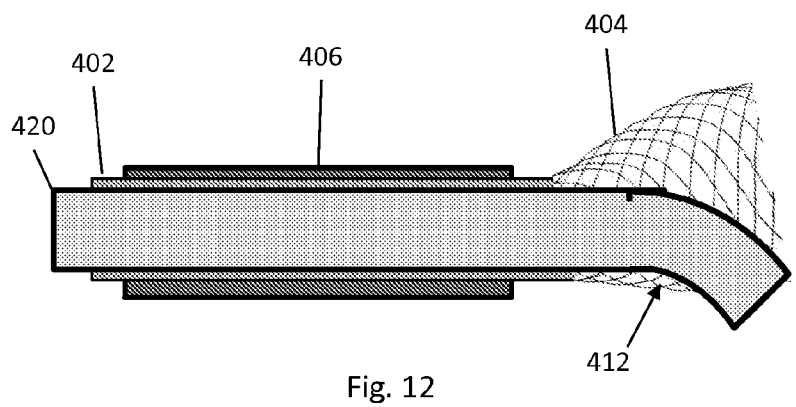
FIG. 12 is a schematic broken side view of the third embodiment of a flow directional infusion device according to the invention, shown in a deployed configuration.
Figure 13:
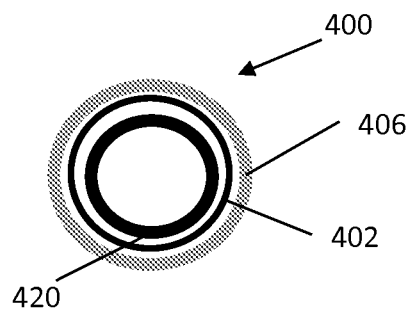
FIG. 13 illustrates the relative positions of the microcatheter and the filter valve of the third embodiment of the flow directional infusion device in the non-deployed configuration.
Figure 15:
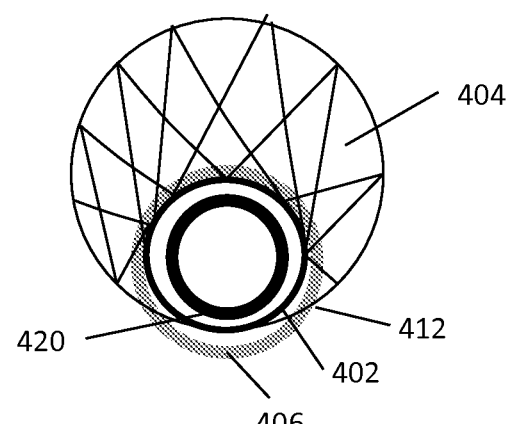
FIG. 15 illustrates a distal end view of the relative positions of the microcatheter and the filter valve of the third embodiment of the flow directional infusion device in the deployed configuration.

Turning now to FIGS. 10 through 15, a third embodiment of an infusion device 400 is shown. The device 400 includes a catheter 402, a filter valve 404 secured to the distal end of the outer catheter 402, as in the second embodiment, and a sleeve (or other catheter) 406 displaceable relative to the filter valve 404. A torqueable or biased microcatheter 420 is provided for advancement through the catheter 402 and filter valve 404. The sleeve 406 retains the filter valve 404 in a closed configuration when the sleeve is located over the filter valve (FIGS. 10, 11 and 13) and permits the filter valve 404 to enter an open configuration when the sleeve 406 is refracted relative to the catheter 402 to release the filter valve (FIGS. 12 and 15). The filter valve 404 preferably includes a lateral opening 412 as described above; i.e., a longitudinal opening along a portion of its length to permit the microcatheter 420 to be advanced external of the filter and into an aneurysm 106. Such opening 412 may be defined by incomplete or uneven extension of the filter valve as rotated about its center such as shown in FIGS. 4A-6B. The device 400 may be advanced into the blood vessel over a guidewire 424.

Figure 14:
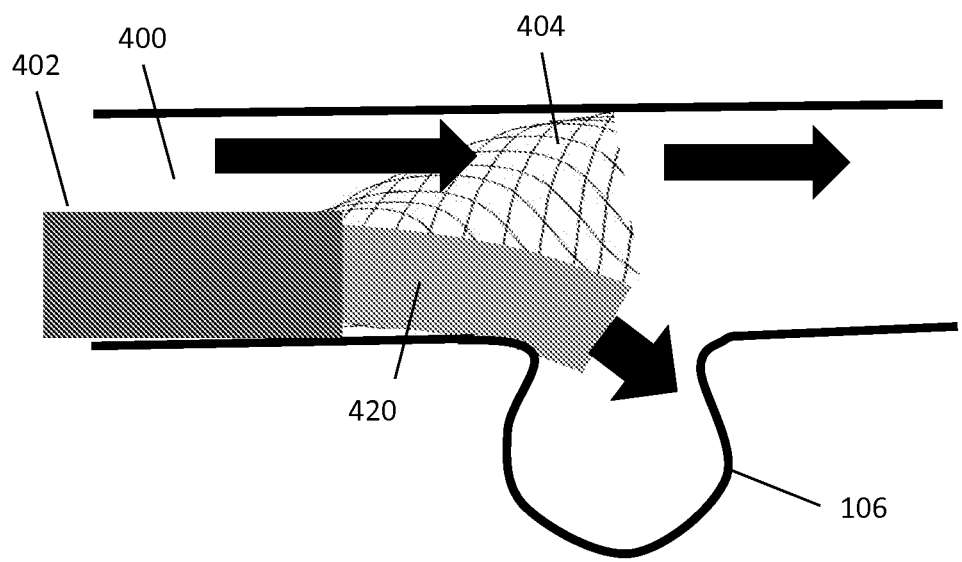
FIG. 14 is a schematic broken side view of the third embodiment of a flow directional infusion device according to the invention, shown deployed within a blood vessel having an aneurysm and configured to inject an embolic agent into the aneurysm.
Figure 16:
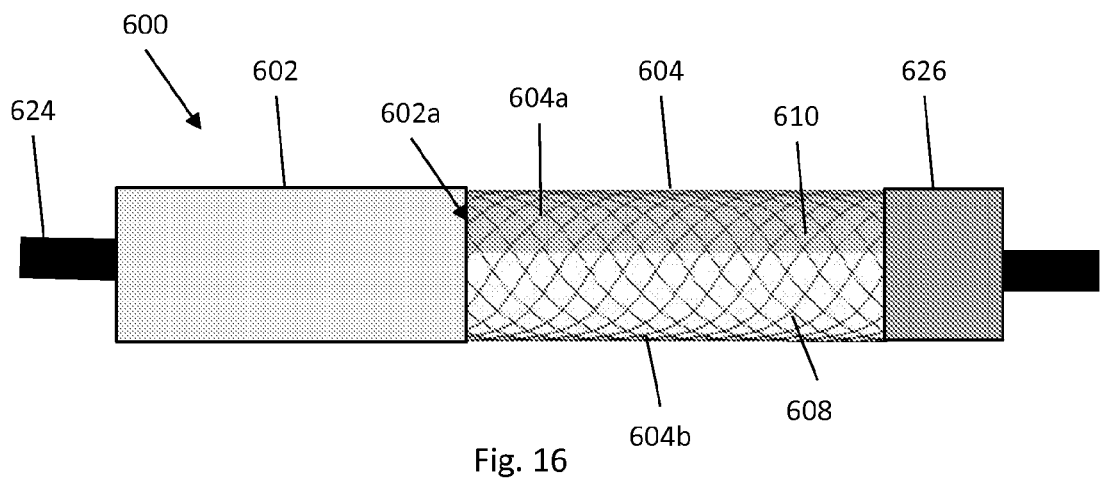
FIG. 16 is a schematic broken side view of a fourth embodiment of a flow directional infusion device according to the invention, shown in a non-deployed configuration.
Figure 17:
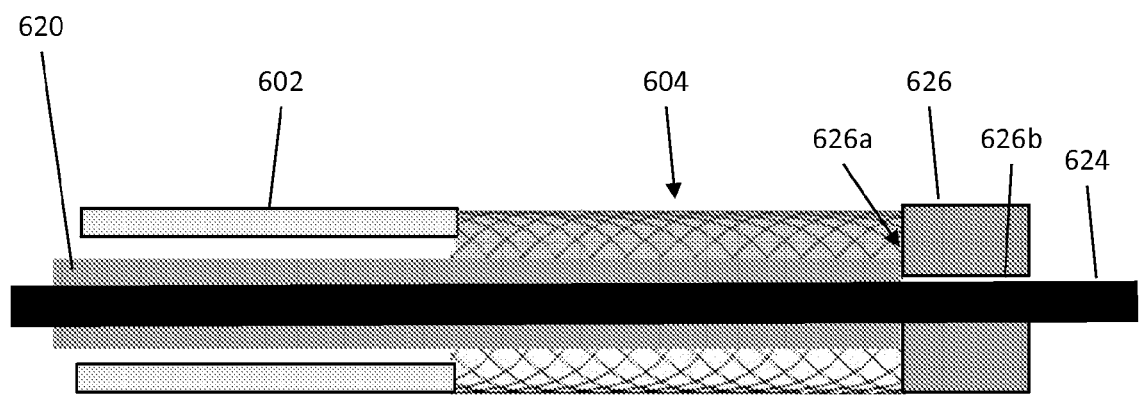
FIG. 17 is a schematic broken longitudinal section view similar to FIG. 16.

Referring to FIGS. 9 and 14, in use, once the infusion device is at the proper location (preferably relatively coextending with the aneurysm 106), the catheter 402 and sleeve 406 are longitudinally displaced relative to each other to effect retraction of the sleeve 406 from over the filter valve 404 and thereby permitting the filter valve to operate in accord with its inherent properties, described above. As shown in FIG. 14, with the filter valve 404 in the deployed configuration, during forward flow of blood, the force of the blood is sufficient to cause the filter valve 404 to automatically radially compress at at least a portion thereof to permit flow of blood past the filter valve such that the filter valve does not obstruct blood flow. During low flow or retrograde flow conditions, the filter valve 404 automatically expands into the valve-open configuration again reaching the vessel wall 102 to thereby prevent upstream flow past the filter valve. With the filter valve 404 in a deployed configuration, the microcatheter 420 is advanced through into the filter valve and laterally into the aneurysm. Once positioned at the aneurysm, an embolic agent is infused through the microcatheter and into the aneurysm. The operation of the filter prevents upstream (retrograde) flow of any embolic agent, yet permit downstream blood flow.

Referring now to FIGS. 16 through 19, a fourth embodiment of an infusion device 600 is shown. The device 600 includes an outer catheter 602, a filter valve 604 secured to and extending from the distal end of the outer catheter 602, and a hub 626 secured the distal ends of the filaments of the filter valve 604. The hub 626 is distally displaced relative to the distal end 602a of the outer catheter 602 and defines a proximal face 626a and a central opening 626b for receiving a guidewire 624. The filter valve includes the braid 608 of first filaments in a preferably tubular form. The filter 610 is applied to the braid between their first and second ends about an axis of rotation less than 360° around the tubular form, and preferably approximately 180° - 300° thereabout. Such application of the filter 610 to the braid 608 thus defines a filtering portion 604a of the filter valve and non-filtering portion 604b of the filter valve. Thus, each of the filtering portion 604a and non-filtering portion 604b extend only a part of the way about the circumference of the device; i.e., each extends in a radially non-uniform manner. In use, as described below, the non-filtering portion 604b is intended to face the aneurysm during injection of an embolic agent. The device is also used in association with a guidewire 624 over which the device 600 is advanceable through the blood vessel to the location of the aneurysm, and a microcatheter 620. The microcatheter 620 is adapted to extend over the guidewire 624 and within the outer catheter 602 during introduction of the device into the blood vessel. The microcatheter may be straight or include a distal pre-bent portion 620a biasing the microcatheter toward the non-filtering portion 604b of the filter valve 604.

Figure 18:
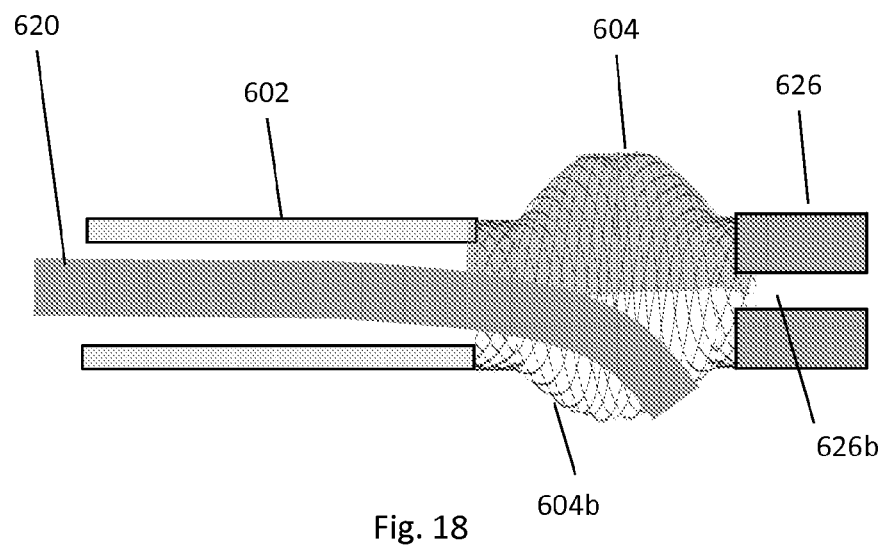
FIG. 18 is a schematic broken side view of the fourth embodiment of a flow directional infusion device according to the invention, shown in a deployed configuration.
Figure 19:
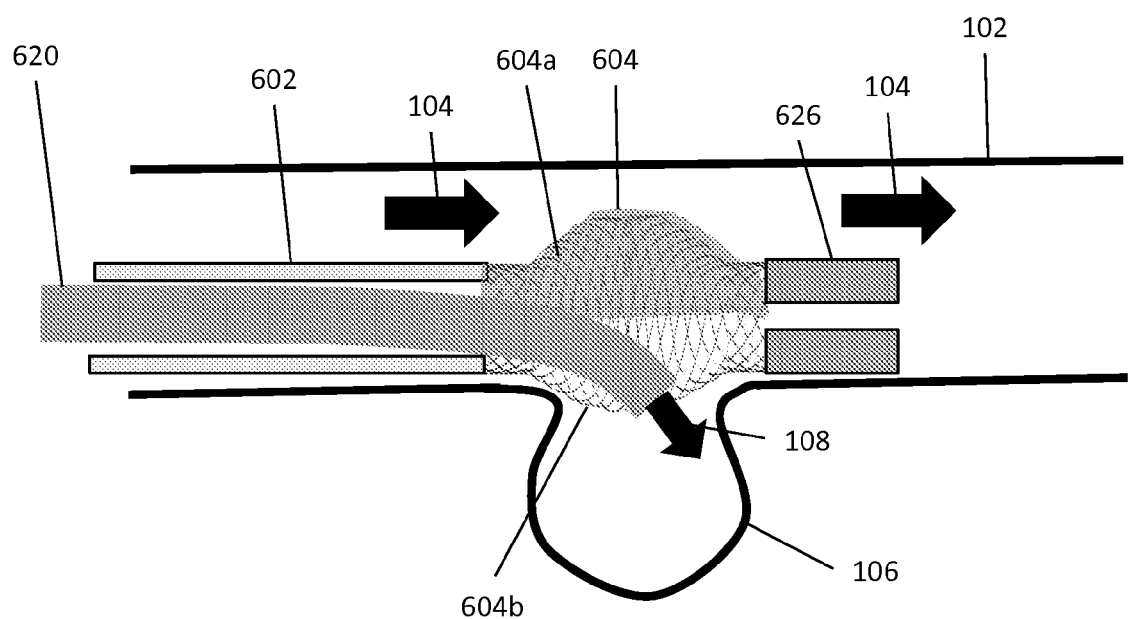
FIG. 19 is a schematic broken side view of the fourth embodiment of a flow directional infusion device according to the invention, shown deployed within a blood vessel having an aneurysm and configured to inject an embolic agent into the aneurysm.
Figure 20:
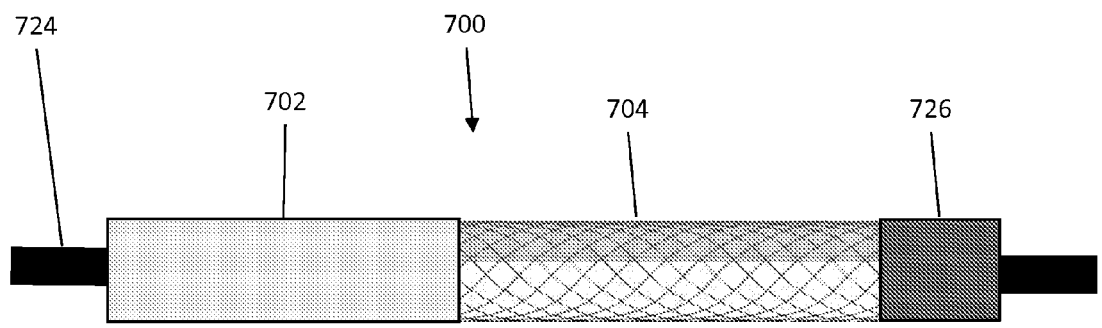
FIG. 20 is a schematic broken side view of a fifth embodiment of a flow directional infusion device according to the invention, shown in a non-deployed configuration.
Figure 21:
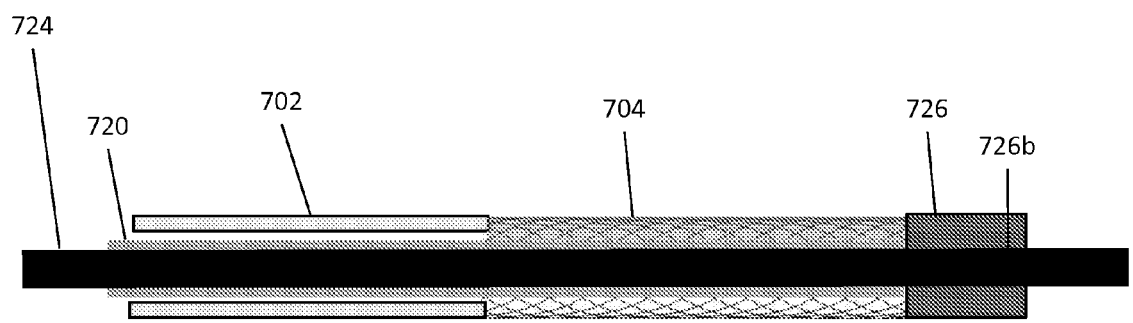
FIG. 21 is a schematic broken longitudinal section view similar to FIG. 20.

The guidewire 624 extends through outer catheter 602, filter valve 604 and bore 626b in the hub 626. With the device 600 arranged relative to the guidewire 624, and the microcatheter 620 extending over the guidewire, the microcatheter is retained in a straightened configuration and can be forcibly butt against the proximal face 626a of the hub 626 to thereby physically displace the hub 626 relative to the distal end 602a of the outer catheter 602. The microcatheter may include longitudinal stiffening to aid in displacement of the hub relative to the catheter. Such stiffening may be along its length or provided at its distal end. It is also appreciated that in the alternative an element other than the microcatheter can be used to retain the elongated configuration of the filter valve during introduction through the blood vessel. This stretches the braid of the filter valve, and the diameter of the tubular form of the filter valve is consequently reduced to thereby facilitate its insertion into the blood vessel. Referring to FIG. 18, after insertion of the filter valve 604 into the blood vessel and location of the filter valve adjacent the aneurysm, the guidewire 624 is removed from the device, the microcatheter is released from engagement with the hub 626, and the filter valve is permitted to radially expand, particularly at its longitudinal center, in accord with its inherent bias. The microcatheter, if pre-bent is directed toward the non-filtering portion 604b of the filter valve. Alternatively, the microcatheter is steerable to be directed toward such non-filtering portion. Once the open end of the microcatheter is oriented toward the non-filtering portion 604b of the filter valve, an embolic agent 108 can be infused through the mesh of the braid and into the aneurysm 106. The filtering portion 604a of the filter operates in accord with the filter valves described above. That is, as seen in FIG. 19, during forward flow of blood 104, the force of the blood is sufficient to cause the filter valve 604 to automatically radially compress at at least a portion thereof to permit the flow of blood past the filter valve such that the filter valve does not obstruct blood flow. During low flow or retrograde flow conditions, the filter valve 604 automatically expands into the valve-open configuration again reaching the vessel wall 102 to thereby prevent upstream flow past the filter valve.

Figure 22:
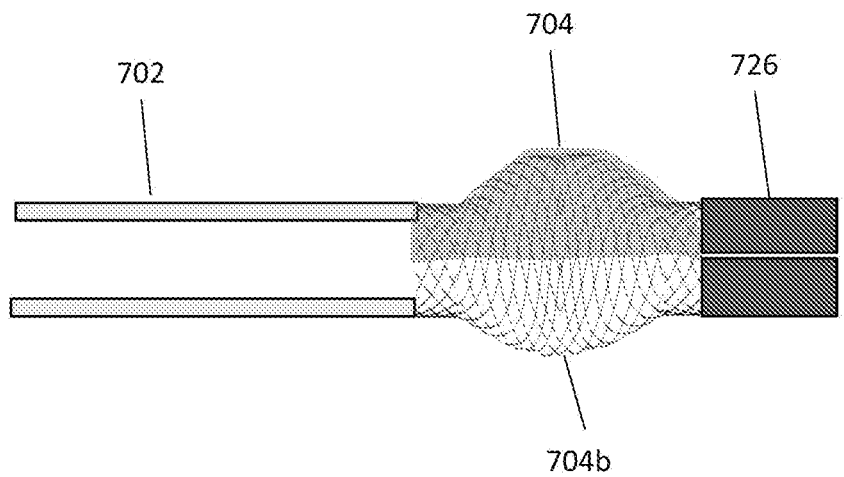
FIG. 22 is a schematic broken side view of the fifth embodiment of a flow directional infusion device according to the invention, shown in a deployed configuration.
Figure 23:
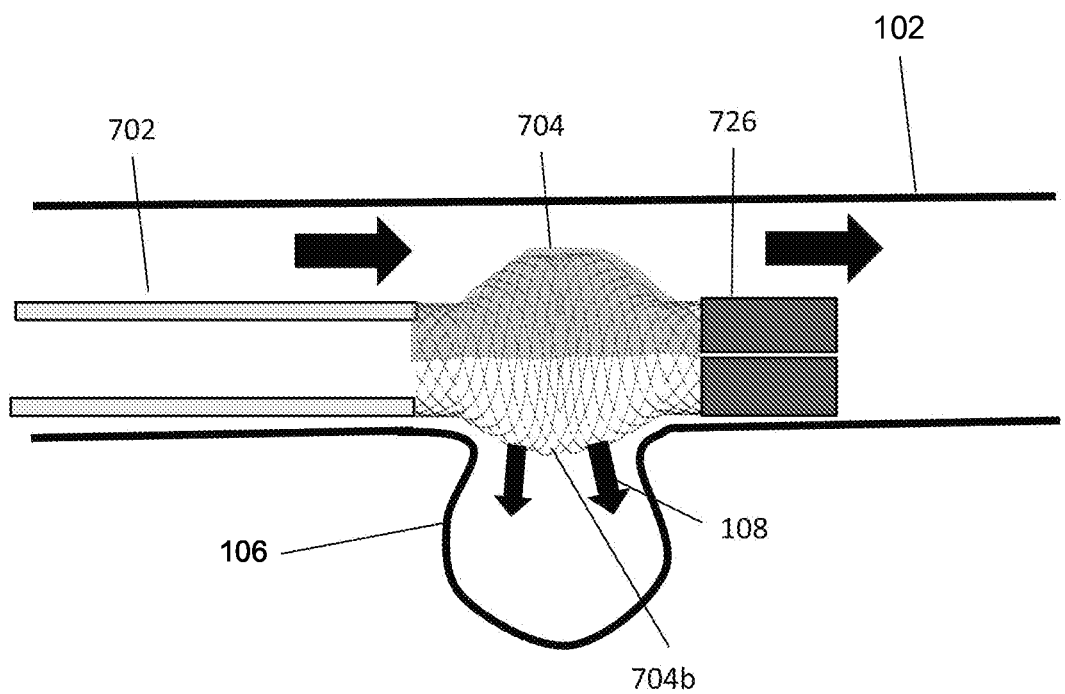
FIG. 23 is a schematic broken side view of the fifth embodiment of a flow directional infusion device according to the invention, shown deployed within a blood vessel having an aneurysm and configured to inject an embolic agent into the aneurysm.

Turning now to FIGS. 20 through 23, a fifth embodiment of a device substantially similar to the fourth embodiment is shown. In that respect, the device 700 includes an outer catheter 702, a filter valve 704 secured to and extending from the distal end of the outer catheter 702, and a hub 726 secured the distal ends of the filaments of the filter valve 704. The device also includes a microcatheter (or other tubular control element) 720 extending through the outer catheter 702 and the filter valve 704 and abutting against the proximal face of the hub 726, and a guidewire 724 extending through the length of the device for guidance through the blood vessel 102. In the fifth embodiment, the device is distinguished relative to the fourth embodiment at the hub 726. In particular, the hub 726 functions as a self-closing valve, with the opening 726b closing once the guidewire 724 is removed (FIG. 22). To this effect, the hub 726 may be elastically compressible to form an at least partial fluid tight barrier, more preferably a substantially fluid tight barrier, and even more preferably a completely fluid tight barrier once the guidewire 724 is removed. This provides at least two advantages. First, once the device is located relative to the aneurysm, the microcatheter 720 can be completely removed from the device 700. That is, the microcatheter 720 is not required to inject the embolic agent. Rather, the embolic agent is injected directly through the outer catheter 702 and through the non-filtering portion 704b of the filter valve 704 and into the aneurysm 106, with the hub 726 in the closed configuration preventing the embolic agent 108 from escaping from the distal end of the device. Second, a longitudinally stiffer microcatheter can be used to longitudinally displace the hub relative to the outer catheter to facilitate advancement of the device into the blood vessel.

Figure 24:
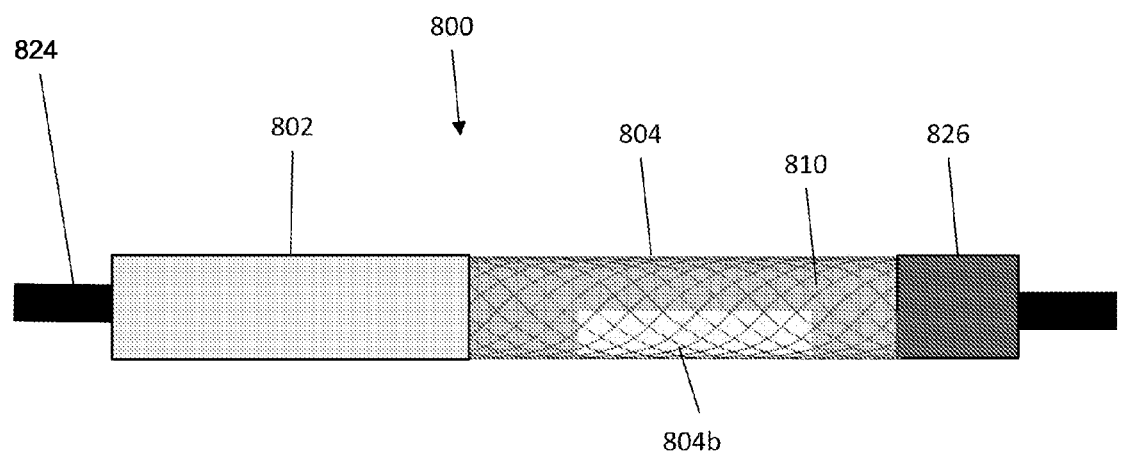
FIG. 24 is a schematic broken side view of a sixth embodiment of a flow directional infusion device according to the invention, shown in a non-deployed configuration.
Figure 25:
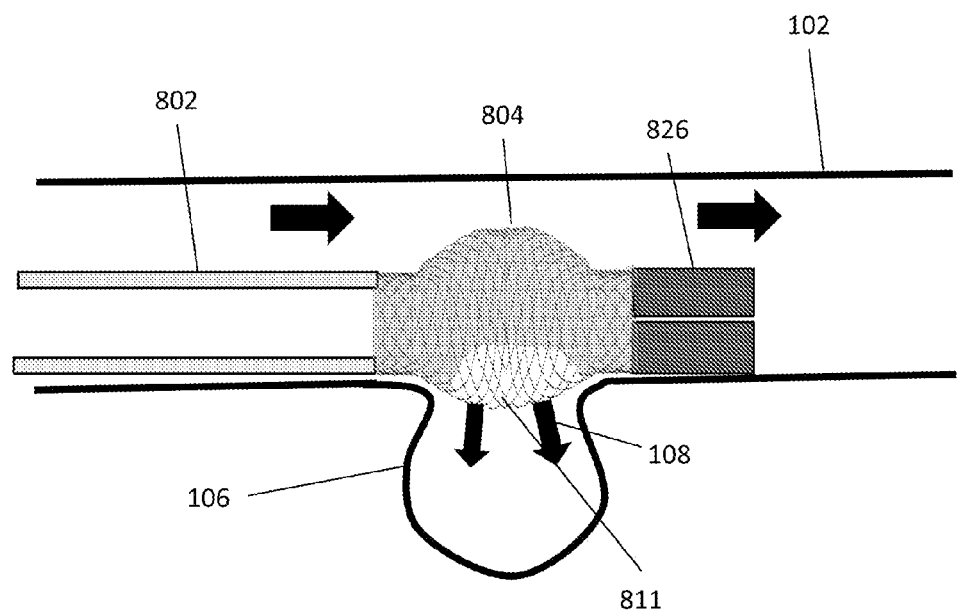
FIG. 25 is a schematic broken side view of the sixth embodiment of a flow directional infusion device according to the invention, shown deployed within a blood vessel having an aneurysm and configured to inject an embolic agent into the aneurysm.

Turning now to FIGS. 24 and 25, a sixth embodiment of a device, substantially similar to the fifth embodiment is shown. In that respect, the device 800 includes an outer catheter 802, a filter valve 804 secured to and extending from the distal end of the outer catheter 802, and a valved or non-valved hub 826 secured the distal ends of the filaments of the filter valve 804. The device also includes a microcatheter (not shown, but described above with respect to microcatheter 720) extending through the outer catheter 802 and the filter valve 804 and abutting against the hub 826, and a guidewire 824 extending through the length of the device for guidance. In the sixth embodiment the device is distinguished relative to the fifth embodiment at the filter valve 804. In particular, filter valve 804 includes a relatively larger portion covered with the filter material 810 including portions extending 360° about the valve. This creates a smaller non-filtering braided portion 804b effecting a more defined or focused exit region 811 at which the embolic agent 108 is infused through the non-filtering portion 804b of the filter valve 804 and into the aneurysm 106.

There have been described and illustrated herein several embodiments of a flow directional infusion device and methods of using the same. While particular embodiments of the invention have been described, it is not intended that the invention be limited thereto, as it is intended that the invention be as broad in scope as the art will allow and that the specification be read likewise. Thus, while the device and method have been described with particular application to infusing an embolic agent for treatment of an aneurysm, it is appreciated that an infusate other than an embolic agent may be infused or injected through the device and that the device may have application beyond treatment of aneurysms. In addition, it is contemplated that aspects of the various embodiments can be combined. It will therefore be appreciated by those skilled in the art that yet other modifications could be made to the provided invention without deviating from its spirit and scope as claimed.

What is claimed is:

1. A flow directional infusion device for reducing reflux of an agent in an infusate in a vessel during a therapy procedure, comprises:
   a) a catheter having a proximal portion and a distal portion with a distal end; and
   b) a composite filter valve located at said distal portion of said catheter, said filter valve having a proximal end fixed to said catheter, and a distal end, said filter valve comprising,
      i) a plurality of elongate polymeric first filaments provided in a braid and together defining a valve, each of said first filaments having a diameter of 0.025 mm to 0.127 mm, said first filaments having a proximal end, a distal end, and a length extending between the proximal and distal ends of the said first filaments, said proximal ends of said first filaments secured relative to each other,
      said valve fully collapsible into an undeployed state, and expandable from said undeployed state into a radially-expanded deployed state by a spring bias of said first filaments, said first filaments extending relative to each other in said braid in a non-bonded state such that they are movable relative to each other as said valve moves from said undeployed state to said deployed state,
      wherein in said deployed state said first filaments cross one another within said braid at an angle of 100° to 150°, and said first filaments have a Young's modulus of elasticity greater than 100 MPa, and
      ii) a filter formed by polymeric second filaments that are integrated with said valve by electrostatically depositing or spinning said second filaments onto the first filaments, said filter defining a pore size not exceeding 500 μm,
      wherein said filter valve expands from said undeployed state to said deployed state in less than one second in an at-rest fluid having a viscosity of 3.2 cP,
      wherein once said filter valve is in said deployed state in the vessel, said filter valve is dynamically movable within the vessel between an expanded valve-open configuration and a collapsed valve-closed configuration depending on local biological fluid flow conditions about said filter valve, and when said filter valve is in said valve-open configuration, said pore size of said filter renders said filter impermeable to the agent of the infusate, and
      said filter valve having a circumferential wall defining an opening located proximal of said distal end of said filter valve for transfer of the infusate from a location within said catheter, through said opening in said circumferential wall of said filter so as to exit the filter valve in a radially non-uniform manner, and to deliver the infusate from said filter valve into the vessel at a location proximal said distal end of said filter valve.

2. The flow directional infusion device according to claim 1, wherein:
   said opening includes a longitudinal break in an outer wall defining of said filter valve.

3. The flow directional infusion device according to claim 2, wherein:
   said longitudinal break extends along said length of said filter valve.

4. The flow directional infusion device according to claim 1, wherein:
said opening includes a circumferential discontinuity along an entire length of said circumferential wall of said filter valve.

5. The flow directional infusion device according to claim 1, wherein:
said opening includes a radial hole between said proximal and distal portions of said filter valve.

6. The flow directional infusion device according to claim 1, wherein:
said distal end of said catheter is radially displaceable relative to said opening.

7. The flow directional infusion device according to claim 6, wherein:
said distal end of said catheter is steerable through said opening.

8. The flow directional infusion device according to claim 6, wherein:
said distal end of said catheter is provided with a predefined radial bias that biases said distal end of said catheter toward said opening.

9. The flow directional infusion device according to claim 1, further comprising:
a second catheter having a distal end, said second catheter extending through and longitudinally displaceable relative to said catheter such that said distal end of said second catheter can be advanced relative to said opening to infuse the infusate through said second catheter and said opening.

10. The flow directional infusion device according to claim 1, further comprising:
a sleeve longitudinally displaceable relative to said filter valve,
wherein when said sleeve is located over said filter valve, said filter valve is retained in said undeployed state, and
when said sleeve is refracted relative to said filter valve, said filter valve automatically enters said deployed state.

11. The flow directional infusion device according to claim 1, wherein:
said filter valve expands to a substantial frustoconical shape.

12. The flow directional infusion device according to claim 1, further comprising:
a hub fixed at said distal end of said filter valve.

13. The flow directional infusion device according to claim 12, further comprising:
a tubular control element extending through said catheter and said filter valve and abutting against a proximal face of said hub, and
a guidewire extending through said tubular control element and beyond a distal portion of said hub.

14. The flow directional infusion device according to claim 13, wherein:
said hub includes a self-closing valve such that when said guidewire is withdrawn out of said hub, said hub forms a fluid barrier at said distal end of said filter valve.

15. A flow directional infusion device for reducing reflux of an embolic agent in an infusate in a vessel during a therapy procedure, comprises:
a) a catheter having a proximal portion and a distal portion with a distal end; and
b) a composite filter valve located at said distal portion of said catheter, said filter valve having a proximal end fixed to said catheter, and a distal end, said filter valve comprising,
i) a plurality of elongate polymeric first filaments provided in a tubular form braid, each of said first filaments having a diameter of 0.025 mm to 0.127 mm, said first filaments having a proximal end, a distal end, and a length extending between the proximal and distal ends of the said first filaments, said proximal ends of said first filaments secured relative to each other and defining a valve,
said valve fully collapsible into an undeployed state, and expandable from said undeployed state into a radially-expanded deployed state by a spring bias of said first filaments, said first filaments extending relative to each other in said braid in a non-bonded state such that they are movable relative to each other as said valve moves from said undeployed state to said deployed state,
wherein in said deployed state said first filaments cross one another within said braid at an angle of 100° to 150°, and said first filaments have a Young's modulus of elasticity greater than 100 MPa, and
ii) a filter formed by polymeric second filaments that are integrated with said valve by electrostatically depositing or spinning said second filaments onto said first filaments, said filter defining a pore size not exceeding 500 μm such that said filter is impermeable to the embolic agent, and said filter applied to said braid of first filaments about an axis of rotation that is less than 360° around said tubular form braid to thereby define a non-filtering portion of said filter valve that is permeable to the embolic agent, said non-filtering portion for transfer of the embolic agent from a location within said catheter, through said non-filtering portion, and to outside said filter valve,
wherein once said filter valve is in said deployed state in the vessel, said filter valve is dynamically movable within the vessel between an expanded valve-open configuration and a collapsed valve-closed configuration depending on local biological fluid flow conditions about said filter valve.

16. The flow directional infusion device according to claim 15, wherein:
said non-filtering portion of said filter valve extends along an entire length of said filter valve.

17. The flow directional infusion device according to claim 15, wherein:
said non-filtering portion of said filter valve extends along less than an entire length of said filter valve.

* * * * *